US006763838B2

United States Patent
Suzuki et al.

(10) Patent No.: US 6,763,838 B2
(45) Date of Patent: Jul. 20, 2004

(54) DEVICE FOR DETECTING A FILLING DENSITY OF FILLER FORMING A ROD-SHAPED ARTICLE

(75) Inventors: Takehiro Suzuki, Tokyo (JP); Yoshiaki Ishikawa, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 52 days.

(21) Appl. No.: 10/339,557

(22) Filed: Jan. 10, 2003

(65) Prior Publication Data

US 2003/0102001 A1 Jun. 5, 2003

Related U.S. Application Data

(63) Continuation of application No. PCT/JP01/05989, filed on Jul. 10, 2001.

(30) Foreign Application Priority Data

Jul. 11, 2000 (JP) .......................... 2000-209788

(51) Int. Cl.[7] .............................. A24C 5/24; A24C 5/18; B07C 5/12
(52) U.S. Cl. ................... 131/280; 131/84.1; 131/905; 131/906; 209/536; 209/535; 356/432; 250/359.1; 250/358.1
(58) Field of Search .................. 131/84.1, 84.4, 131/905, 906, 909, 280, 84.3, 84.2; 356/432, 433, 237.1, 434, 435, 445; 209/535, 536; 250/336.1, 358.1, 359.1

(56) References Cited

U.S. PATENT DOCUMENTS

| 4,616,139 A | 10/1986 | Heitmann |
| 4,986,285 A | 1/1991 | Radzio |
| 5,651,041 A | 7/1997 | Moller et al. |
| 6,421,126 B1 * | 7/2002 | Kida et al. .................. 356/432 |

FOREIGN PATENT DOCUMENTS

| JP | 7-308180 A | 11/1995 |
| JP | 8-2288 B2 | 1/1996 |
| JP | 11-344446 A | 12/1999 |

* cited by examiner

*Primary Examiner*—Dionne A. Walls
(74) *Attorney, Agent, or Firm*—Birch, Stewart, Kolasch & Birch, LLP

(57) ABSTRACT

A device for detecting a shredded tobacco filling density in a tobacco rod includes four light sources (18, 20, 22 and 24) arranged separately from one another at an angle of 45° around a tobacco rod (T) and causing infrared rays to enter the tobacco rod (T), two light receivers (26 and 28) disposed around the tobacco rod (T) on a side opposite to the four light sources and arranged separately from each other at an angle of 90°, and a measuring device (44) for measuring the shredded tobacco filling density in the tobacco rod (T) based on outputs from the light receivers (26 and 28).

11 Claims, 5 Drawing Sheets

DEVICE FOR DETECTING A FILLING DENSITY OF FILLER FORMING A ROD-SHAPED ARTICLE

This is a Continuation Application of PCT Application No. PCT/JP01/05989, filed on Jul. 10, 2001.

TECHNICAL FIELD

The present invention relates to a device for detecting a filling density of filler in a rod-shaped article and, more specifically, to a detecting device suitable for detecting a shred tobacco filling density in a tobacco rod produced by a cigarette manufacturing machine.

BACKGROUND ART

This kind of filling density detecting device conventionally uses radial rays. More specifically, the detecting device emits radial rays toward a tobacco rod, and detects the filling density of shredded tobacco, based on the degree of attenuation of the radial rays passing through the shredded tobacco.

The use of radial rays requires a strict control system as a safety measure, and it is not easy to handle the radial ray-type detecting device.

In view of this, filling density detecting devices using infrared rays in place of radial rays have been developed, and an example thereof is disclosed in Examined Japanese Patent Publication No. 8-2288. This known detecting device comprises a plurality of infrared light sources and a plurality of light receivers. The light sources and the light receivers are disposed along a horizontal delivery path for a tobacco rod in a cigarette manufacturing machine. The delivery path extends from a wrapping section of the cigarette manufacturing machine.

In the detecting device, infrared rays are irradiated from each light source toward the outer peripheral surface of tobacco rod, and the infrared rays which have been transmitted through the tobacco rod or diffused in gaps in the tobacco rod are received by each light receiver. Then, based on the quantity of the received infrared rays, a density signal indicative of the shredded tobacco filling density is output.

The output level of the density signal is higher in a diffusion type in which infrared rays are diffused than a transmission type in which infrared rays are transmitted, and a detecting device of the diffusion type is suitable for measuring the shredded tobacco filling density. Therefore, the filling density of the shredded tobacco in the tobacco rod may be measured by using the diffusion type detecting device, and in this case soft spots in the tobacco rod can also be detected. The soft spot here means a part of the tobacco rod having a shredded tobacco filling density lower than a reference range.

In the diffusion type detecting device (cf. FIG. 6) disclosed in the above publication, the infrared light sources and the light receivers are alternately disposed in the circumferential direction of the tobacco rod. Moreover, each light source and each light receiver are disposed so as to face another light source and another light receiver, respectively, across the tobacco rod.

For this reason, two opposed light sources irradiate only the same spot in the tobacco rod, so that the regions irradiated with infrared rays are narrow as viewed in the cross section of the tobacco rod. Accordingly, the known detecting device is low in diffusion efficiency of infrared rays in the tobacco rod, and thus is not capable of detecting the shredded tobacco filling density with high accuracy throughout the whole cross-sectional area of the tobacco rod.

Furthermore, since one pair of opposed light sources is disposed in a horizontal plane, the infrared rays incident from these light sources into the tobacco rod pass directly through the shredded tobacco, which is in a substantially vertically layered state, in the tobacco rod. Consequently, the known detecting device is not capable of satisfactorily diffusing infrared rays in the tobacco rod, showing low soft-spot detection accuracy.

DISCLOSURE OF THE INVENTION

An object of the present invention is to provide a detecting device capable of detecting with high accuracy a filling density of filler in a rod-shaped article by using inspection light except radial rays, which can be controlled easily.

The above object can be achieved by a detecting device of the present invention, comprising light incidence means for making inspection light incident into a rod-shaped article, light-receiving means for receiving the inspection light from the rod-shaped article, and measuring means for measuring a filling density of filler based on an output from the light-receiving means. The light incidence means has a plurality of light sources disposed in a predetermined arcuate area surrounding the rod-shaped article adjacently to each other in a circumferential direction of the rod-shaped article and causing the inspection light to enter the rod-shaped article in an identical cross section of the rod-shaped article. The light receiving means has at least one light receiver disposed in an area other than the arcuate area in the circumferential direction of the rod-shaped article so as not to face any of the light sources, receiving the inspection light emitted from the rod-shaped article along the cross section, and generating a signal indicative of the received-light quantity.

According to the above detecting device, the inspection light incident from each light source into the rod-shaped article is reflected by the filler in the rod-shaped article, and as the reflection is repeated, the inspection light is diffused in gaps in the rod-shaped article. Then, the diffused inspection light is emitted from the rod-shaped article and received by the light receiver. The light receiver supplies a signal corresponding to the quantity of the received inspection light to the measuring means, which measures the filling density of the filler based on the received signal.

Beams of the inspection light from the light sources enter the rod-shaped article in respective different directions, thereby irradiating a wide area of the rod-shaped article as viewed in the same cross section and diffusing uniformly throughout substantially the whole area of the cross section. As a result, the quantity of the diffused inspection light received by the light receiver represents an accurate density of the filler in the rod-shaped article.

The light incidence means may include four light sources arranged separately from one another at a predetermined angle in the circumferential direction of the rod-shaped article. The light receiving means may include two light receivers which are also arranged separately from each other at a predetermined angle in the circumferential direction of the rod-shaped article.

Where the rod-shaped article is a tobacco rod delivered in a horizontal direction from a wrapping section of a cigarette manufacturing machine, the detecting device measures a shredded tobacco filling density in the tobacco rod. In this case, it is preferable that each light source of the detecting device causes the inspection light to enter the tobacco rod in a direction other than the horizontal direction. As a consequence of such arrangement, the inspection light never passes through gaps of the shredded tobacco in the tobacco rod without being reflected, so that only the diffused inspection light is emitted from the tobacco rod.

More specifically, the four light sources are arranged separately from one another at an angle of 45°, while the two light receivers are arranged separately from each other at an angle of 90°. More preferably, two of the light sources are disposed adjacently to each other with a vertical longitudinal section of the rod-shaped article therebetween, and the remaining two light sources are disposed adjacently to each other with a horizontal longitudinal section of the rod-shaped article therebetween. With this arrangement, the inspection light from the light sources is diffused uniformly in the tobacco rod, which enables the light receivers to satisfactorily receive the inspection light emitted from the tobacco rod.

In this case, one of the light receivers may be disposed on the vertical longitudinal section, and the other may be disposed on the horizontal longitudinal section.

The light sources and the light receivers may be mounted on a holder surrounding the tobacco rod, and the light sources and the light receivers in this instance form one detecting unit.

Each light source is capable of making infrared rays as the inspection light incident into the tobacco rod. Infrared rays are excellent in diffusibility within the tobacco rod and can be easily controlled.

BEST MODE OF CARRYING OUT THE INVENTION

Figure 1:
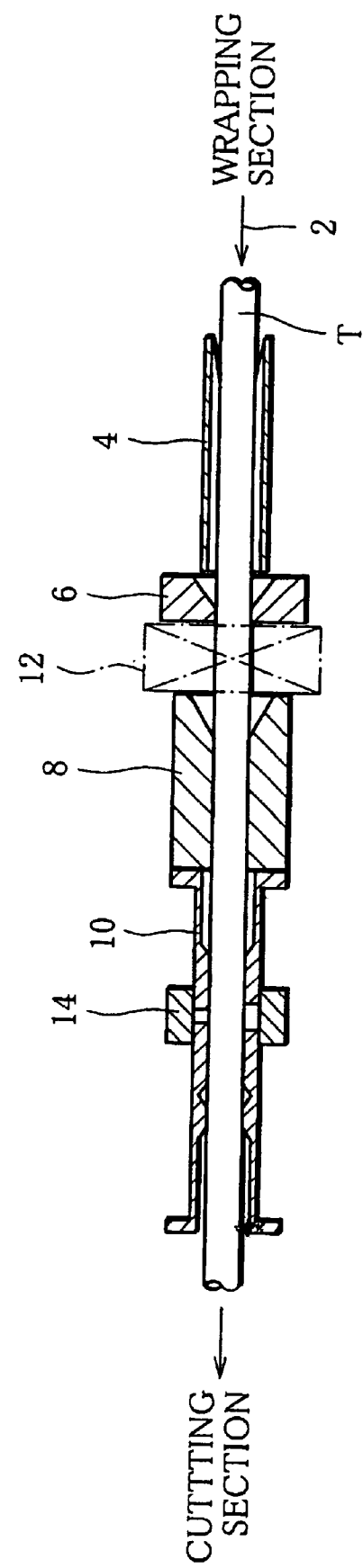
FIG. 1 is a view showing a location of a detecting unit of the present invention in the case where the detecting unit is incorporated into a cigarette manufacturing machine.

FIG. 1 shows a part of a cigarette manufacturing machine, namely, a horizontal delivery path 2 for a tobacco rod T, the delivery path 2 extending from a wrapping section and through a cutting section of the machine.

The wrapping section wraps in paper a tobacco stream in which shredded tobacco is vertically layered, to form the tobacco rod T. The shredded tobacco in the tobacco rod T substantially maintains its vertically layered state. On the other hand, the cutting section of the machine cuts the tobacco rod T into a predetermined length to form cigarette rods, which have a length equivalent to two cigarettes used in the manufacture of filter cigarettes.

The delivery path 2 includes rod guides 4, 6, 8 and 10 allowing the tobacco rod T to pass therethrough, and each rod guide is in the shape of a tube or a ring. The rod guides 4, 6, 8 and 10 are sequentially disposed in a delivery direction of the tobacco rod T.

The rod guide 10 on the cutting section side is in the shape of a tube, and a detecting unit 14 of a diffusion type according to an embodiment of the invention is disposed in the middle of the rod guide 10.

There is provided a predetermined space between the rod guides 6 and 8, and disposed in the space is the aforementioned known detecting unit 12 of the diffusion type. The detecting unit 12 is used to evaluate output results of the detecting unit 14.

Figure 2:
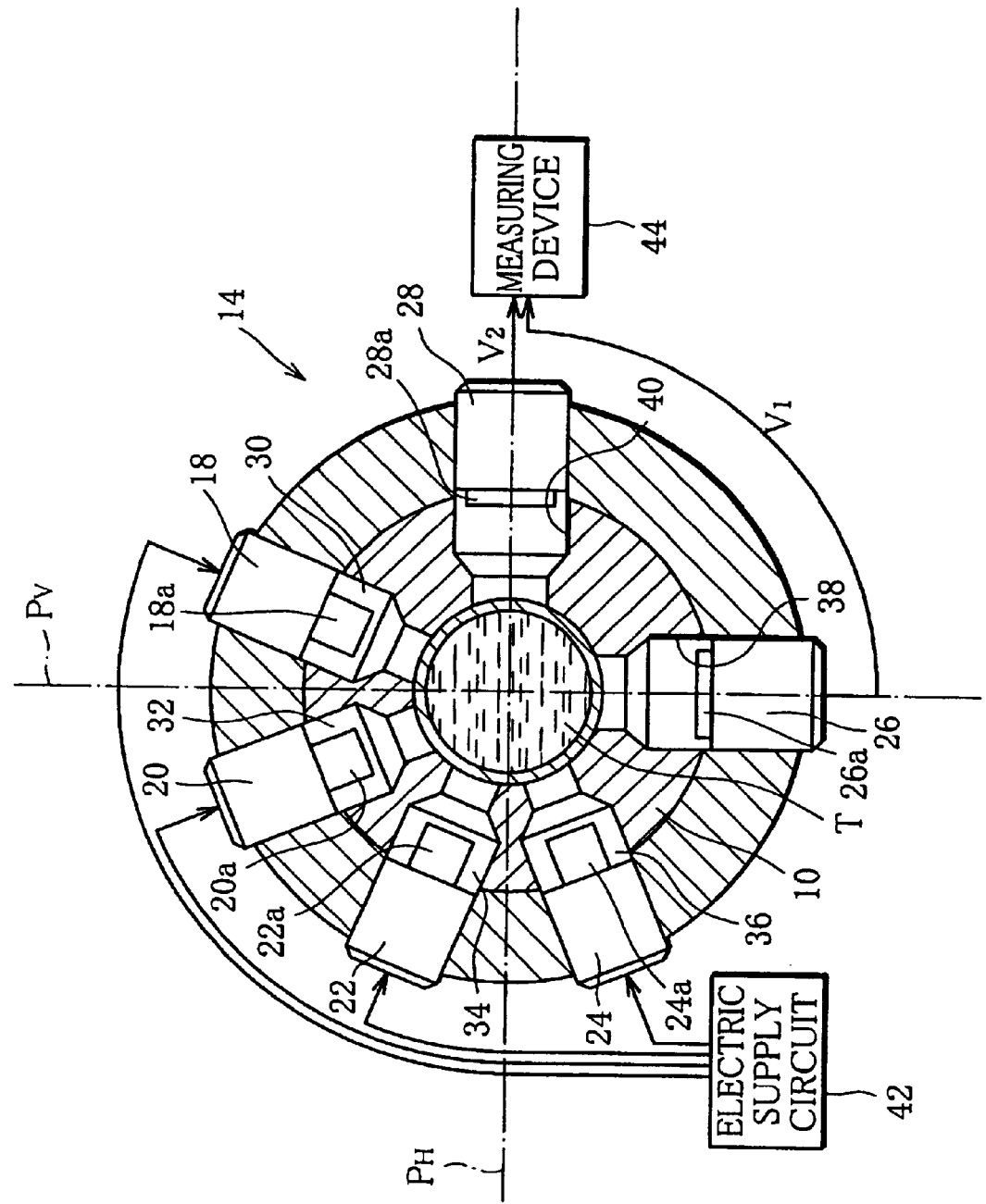
FIG. 2 is a cross-sectional view of the detecting unit of FIG. 1.

FIG. 2 illustrates details of the detecting unit 14, which comprises a ring-shaped holder 16 surrounding an outer periphery of the rod guide 10. The holder 16 comprises four light sources 18, 20, 22 and 24, and two light receivers 26 and 28. Each light source is a halogen lamp that emits infrared rays, whereas each light receiver is a photoelectric converter.

As is obvious from FIG. 2, the four light sources and the two light receivers are located on a same cross section of the holder 16. More specifically, the light sources 18, 20, 22, and 24 are arranged at intervals in a circumferential direction of the holder 16 and have infrared-ray emitting portions 18a, 20a, 22a and 24a projecting into the rod guide 10. The emitting portions are separately arranged at an angle of 45° in the circumferential direction of the tobacco rod T passing through the rod guide 10.

Therefore, the rod guide 10 is provided with radial holes 30, 32, 34 and 36, which are also separately arranged at an angle of 45° in the circumferential direction of the rod guide 10 and receive the emitting portions of their corresponding light sources 18, 20, 22 and 24. The radial holes 30, 32, 34 and 36 open in an inner peripheral surface of the rod guide 10, allowing the infrared rays from the light sources 18, 20, 22 and 24 to be irradiated on an outer peripheral surface of the tobacco rod T through their respective radial holes.

As is apparent from FIG. 2, the light sources 18 and 20 are arranged apart from each other with a vertical longitudinal section $P_V$ of the holder 16 therebetween, whereas the light sources 22 and 24 are arranged apart from each other with a horizontal longitudinal section $P_H$ of the holder 16 therebetween. Accordingly, the infrared-ray emitting direction of each light source intersects the layering direction of the shredded tobacco in the tobacco rod T.

On the other hand, the light receivers 26 and 28 are disposed in an area opposite to the light sources 18, 20, 22 and 24, as viewed in a diametrical direction of the holder 16. More specifically, the light receivers 26 and 28 are located on the longitudinal sections $P_V$ and $P_H$, respectively, and have light-receiving portions 26a and 28a projecting into the rod guide 10.

To this end, the rod guide 10 further has two radial holes 38 and 40 for receiving the light-receiving portions of their corresponding light receivers. The radial holes 38 and 40 also open in the inner peripheral surface of the rod guide 10, and thus the light-receiving portions of the light receivers 26 and 28 can receive the infrared rays which have passed through the tobacco rod T.

As is clear from FIG. 2, since the light receivers 26 and 28 are however located opposite to none of the light sources 18, 20, 22 and 24, the infrared rays incident from the light sources 18, 20, 22 and 24 into the tobacco rod T do not directly reach the light receivers 26 and 28 after transmitting through the shredded tobacco or gaps thereof in the tobacco rod T. Here, a void ratio in the tobacco rod T is in a range from about 65% to 70%.

As illustrated in FIG. 2, each of the light sources 18, 20, 22 and 24 is electrically connected to an electric supply circuit 42, while each of the light receivers 26 and 28 is electrically connected to a measuring device 44. When power is supplied from the electric supply circuit 42 to the light sources 18, 20, 22 and 24, each light source emits infrared rays through its emitting portion, and the infrared rays are introduced into the tobacco rod T through the respective radial holes 30, 32, 34 and 36. The infrared rays thus introduced are diffused into gaps of the shredded tobacco in the tobacco rod T while being reflected by the shredded tobacco, and then emitted from the tobacco rod T through the radial holes 38 and 40 to be received by the light-receiving portions of the light receivers 26 and 28.

The light receivers 26 and 28 supply electric signals $V_1$ and $V_2$ to the measuring device 44, respectively. The electric signals $V_1$ and $V_2$ are proportional to the respective quantities of the infrared rays received. Based on the electric signals $V_1$ and $V_2$ from the light receivers 26 and 28, the measuring device 44 generates a density signal $S_D$ indicative of a shredded tobacco filling density in the tobacco rod T and sends the signal to the cigarette manufacturing machine.

For the measuring device 44, a measuring device disclosed in the above-mentioned publication may be used, and therefore a detailed explanation of the measuring device 44 is omitted.

Figure 3:
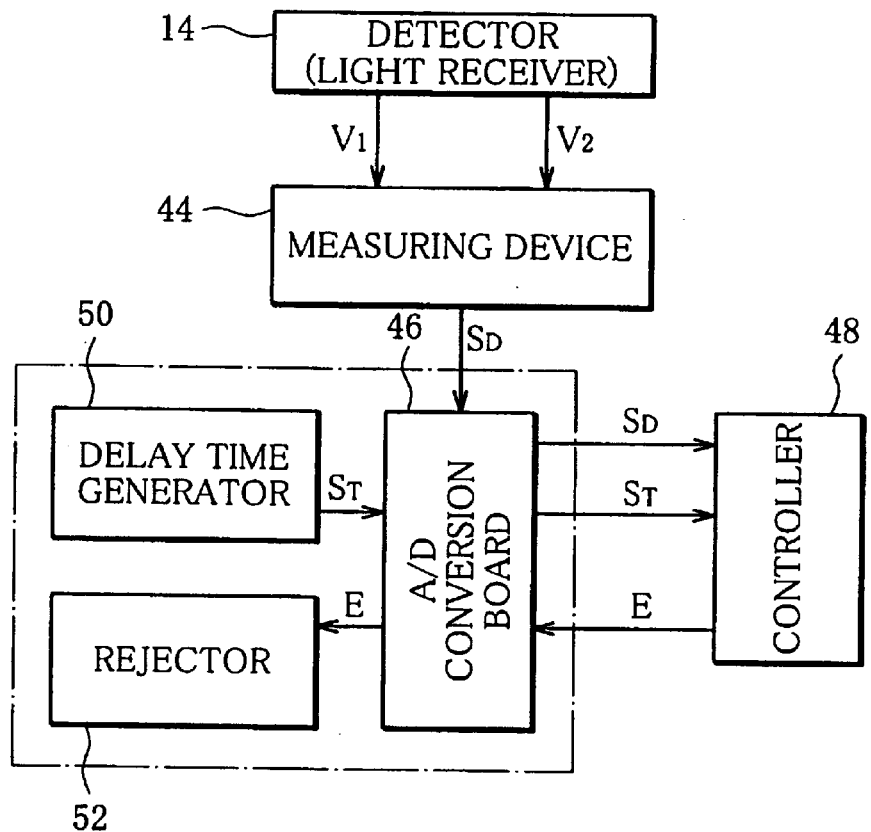
FIG. 3 is a diagram showing a circuit for controlling a rejecting device of the machine by means of the detecting unit of FIG. 1.

As shown in FIG. 3, the density signal $S_D$ sent from the measuring device 44 is supplied to a controller 48 via an A/D conversion board 46 of the cigarette manufacturing machine, the controller 48 including a microcomputer. Meanwhile, delay time $S_T$ is supplied from a delay time generator 50 of the machine to the controller 48 via the A/D conversion board 46.

The delay time generator 50 calculates the delay time $S_T$, based on a distance from the detecting unit 14 to a cigarette rod rejecting device 52 arranged on a downstream side of the cutting section and a current delivery speed of the tobacco rod T, namely, the cigarette rods. The delay time $S_T$ represents the time required for a part of the tobacco rod T which has passed the detecting unit 14 to reach the rejecting device 52 as a cigarette rod.

On receiving the density signal $S_D$, the controller 48 compares the density signal $S_D$ with a reference range. If the density signal $S_D$ is smaller than the reference range, that is, if the shredded tobacco filling density is too much lower than a reference filling density, the controller 48 judges that there exists a soft spot in the tobacco rod T, which is lower in the shredded tobacco filling density, and supplies a rejection signal E to the rejecting device 52 via the A/D conversion board 46 after the lapse of the delay time $S_T$ from the determination time.

As soon as the rejecting device 52 receives the rejection signal E, the rejecting device 52 starts immediately and rejects the cigarette rod including the soft spot to outside the delivery path 2.

Figure 4:
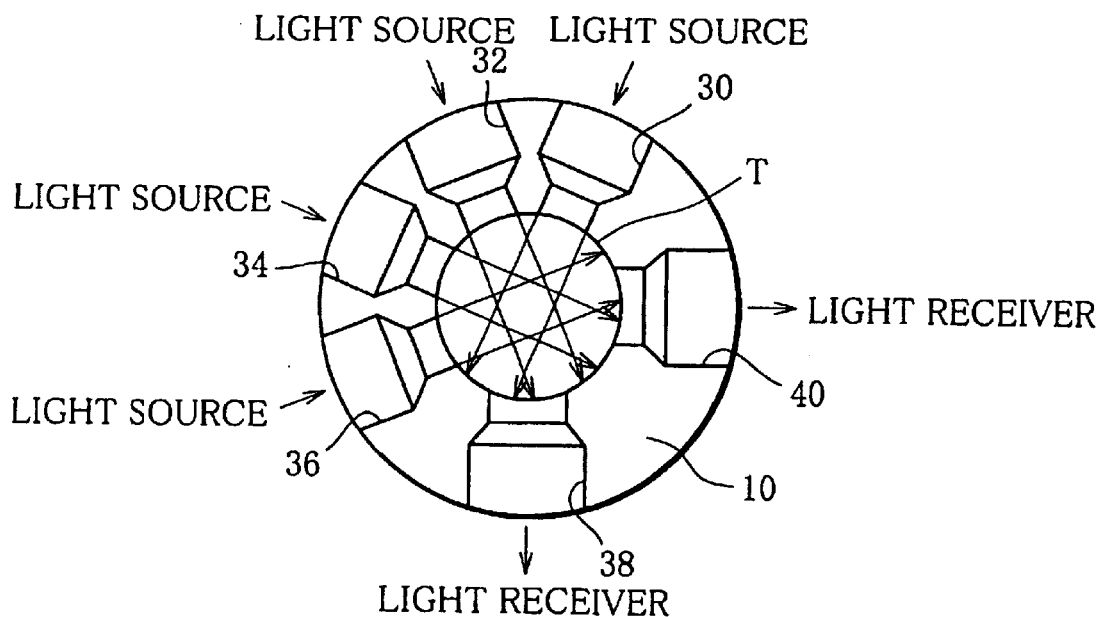
FIG. 4 is a schematic view showing an incidence area of infrared rays incident from individual light sources into a tobacco rod.

As described before, since the four light sources 18, 20, 22 and 24 are separated from one another at an angle of 45° in the circumferential direction of the tobacco rod T, the infrared rays from the light sources enter the tobacco rod T from an outer peripheral region spanning about 135°, as viewed in the circumferential direction of the tobacco rod T. Therefore, as is obvious from FIG. 4, the infrared rays incident into the tobacco rod T are directed to the inside of the tobacco rod T so as to cover substantially the whole cross section of the tobacco rod T. The infrared rays introduced into the tobacco rod T are reflected by the shredded tobacco inside the rod, and the reflection is repeated, so that the infrared rays are uniformly diffused in gaps in the tobacco rod T.

The infrared rays uniformly diffused in the tobacco rod T leak out through the radial holes 38 and 40 of the rod guide 10, and the leaked-out infrared rays are received by the light receivers 26 and 28. Since the infrared rays received by the light receivers 26 and 28 have been uniformly diffused in the tobacco rod T, a received-light level of the infrared rays received by the light receivers 26 and 28 indicates an accurate shredded tobacco filling density, which makes it possible to detect soft spots in the tobacco rod T with high accuracy.

The infrared rays from the light sources 18, 20, 22 and 24 do not horizontally enter the tobacco rod T, so that the infrared rays do not pass directly through gaps in the tobacco rod T to travel toward the light receivers 26 and 28. As a result, the light receivers 26 and 28 can receive only the infrared rays which have been diffused in the tobacco rod T, and therefore the received-light quantity of the infrared rays received by the light receivers 26 and 28 represents an accurate shredded tobacco filling density.

Figure 5:
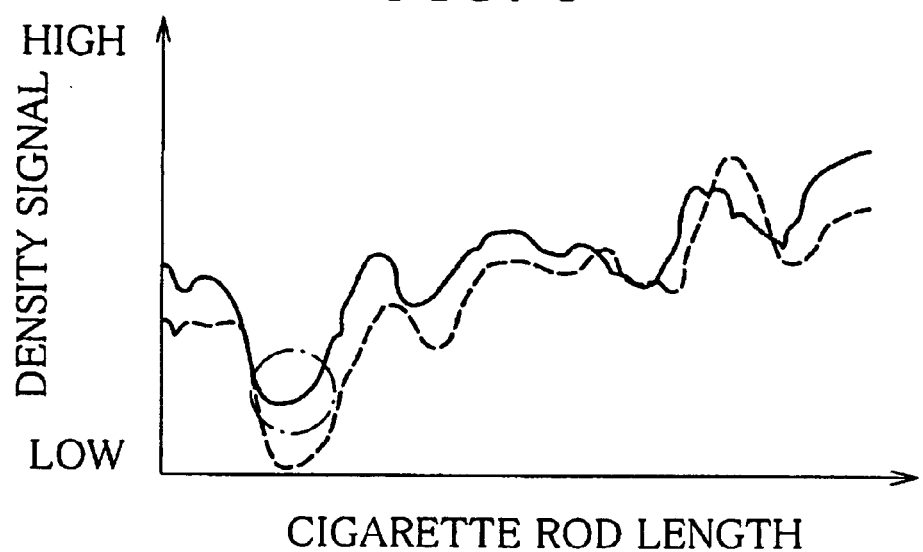
FIGS. 5 to 7 are graphs each showing results of comparison in detecting performances of the detecting unit of the present invention and a known detecting unit.
Figure 6:
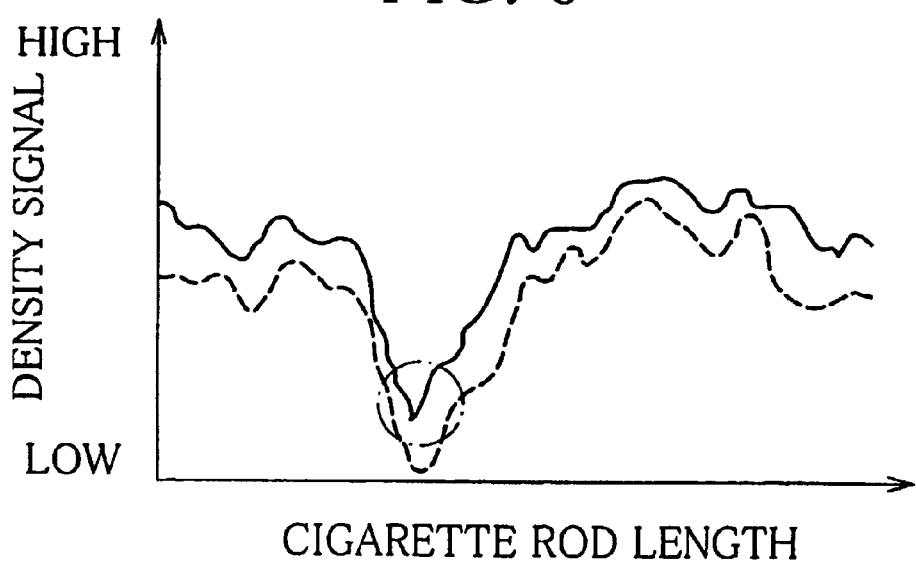
Figure 7:
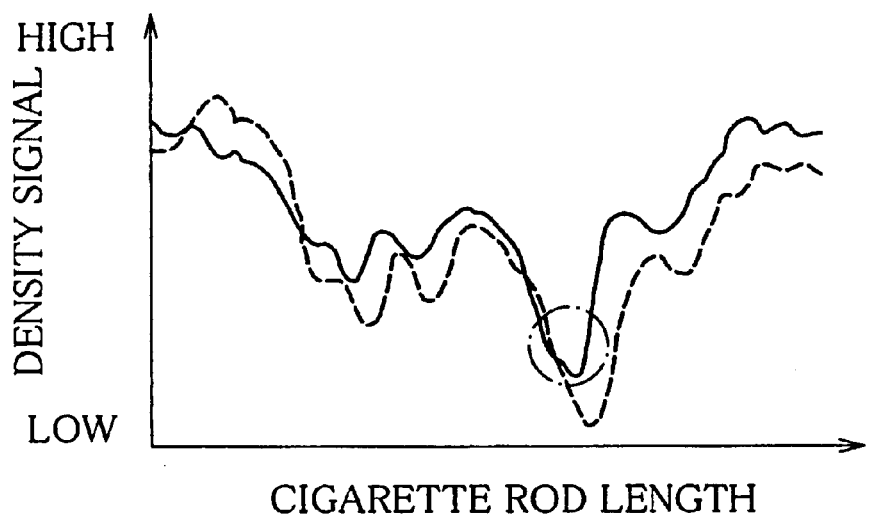

FIGS. 5 to 7 show the results of measurement of the shredded tobacco filling density in the cigarette rod, measured by using the detecting unit 14 of the present invention and the detecting unit 12 of the aforementioned publication at the same time. In FIGS. 5 to 7, the solid line indicates a waveform of the density signal obtained using the detecting unit 14 of the invention, while the dashed line indicates a waveform of the density signal obtained by using the known detecting unit 12.

As is clear from FIGS. 5 to 7, compared with the case where the detecting unit 12 disclosed in the publication is used, the detecting unit 14 of the present invention shows a generally higher output level of the density signal, permitting higher-accuracy measurement of the filling density. In FIGS. 5 to 7, dot-and-dash circles indicate the presence of soft spots.

The present invention is not limited to the above-mentioned embodiment, but may be modified in various ways.

For instance, the number of the light sources and that of the light receivers are not limited to the exemplified ones.

Further, the detecting device of the present invention may be used not only for detecting soft spots but for measuring an average filling density in the cigarette rod. In this case, based on the measurement result of the average filling density, a trimming device for the tobacco stream can be controlled. The trimming device is disposed on an upstream side of the wrapping section and adjusts the thickness of the shredded tobacco layer of the tobacco stream.

Figure 8:
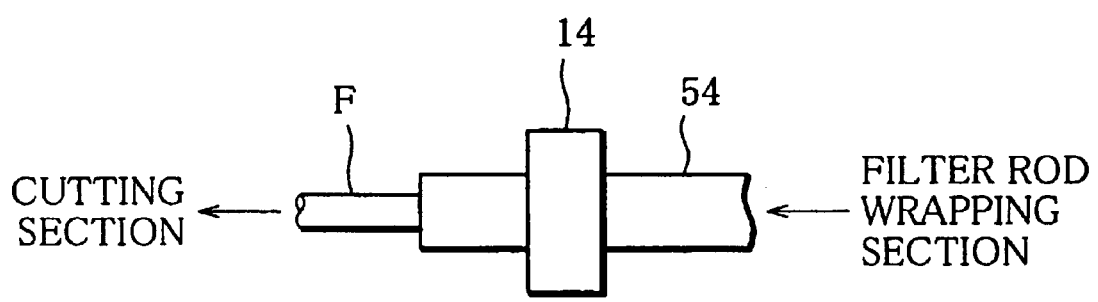
FIG. 8 is a view showing an example in which the detecting unit of the present invention is incorporated into a filter rod manufacturing machine.

Moreover, the detecting device of the present invention may be used to detect the filling density of other fillers than shredded tobacco. For example, it is also possible to incorporate the detecting device into a filter rod manufacturing machine as illustrated in FIG. 8. The filter rod manufacturing machine produces a filter rod F by wrapping a fibrous filter material in paper at its wrapping section, whose structure is similar to that of the wrapping section of the cigarette manufacturing machine.

In this case, the detecting unit 14 is disposed on a rod guide 54 for guiding the filter rod F delivered in a horizontal direction from the wrapping section toward the cutting section, and detects the filling density of the filter material in the filter rod F in the same manner.

What is claimed is:

1. A device for detecting a filling density of filler forming a rod-shaped article, comprising:

light incidence means for causing inspection light to enter the rod-shaped article, said light incidence means including a plurality of light sources disposed in a predetermined arcuate area surrounding the rod-shaped article adjacently to each other in a circumferential direction of the rod-shaped article and causing the inspection light to enter the rod-shaped article in an identical cross section of the rod-shaped article;

light-receiving means for receiving the inspection light from the rod-shaped article, said light-receiving means including at least one light receiver disposed in an area other than said arcuate area in the circumferential direction of the rod-shaped article so as not to face any of said light sources, said light receiver receiving the inspection light emitted from the rod-shaped article along said cross section, and generating a signal indicative of the received-light quantity; and measuring means for measuring a filling density of the filler based on the signal from the light-receiving means.

2. The device according to claim 1, wherein said light incidence means includes four light sources arranged separately from one another at a predetermined angle in the circumferential direction of the rod-shaped article, and said light-receiving means includes two light receivers arranged separately from each other at a predetermined angle in the circumferential direction of the rod-shaped article.

3. The device according to claim 2, wherein the rod-shaped article is a filter rod delivered in a horizontal direction from a wrapping section of a filter rod manufacturing machine, and said device detects a filling density of a filter material in the filter rod.

4. The device according to claim 2, wherein the rod-shaped article is a tobacco rod delivered in a horizontal direction from a wrapping section of a cigarette manufacturing machine, and said device measures a shredded tobacco filling density in the tobacco rod.

5. The device according to claim 4, wherein said each light source causes the inspection light to enter the tobacco rod from a direction other than a horizontal direction.

6. The device according to claim 4, wherein said each light source causes infrared rays as the inspection light to enter the tobacco rod.

7. The device according to claim 5, wherein said four light sources are arranged separately from one another at an angle of 45°.

8. The device according to claim 7, wherein said two light receivers are arranged separately from each other at an angle of 90°.

9. The device according to claim 7, wherein two of said light sources are disposed adjacently to each other with a vertical longitudinal section of the rod-shaped article therebetween, and the remaining light sources are disposed adjacently to each other with a horizontal longitudinal section of the rod-shaped article therebetween.

10. The device according to claim 9, wherein one of said light receivers is disposed on said vertical longitudinal section, and the other is disposed on said horizontal longitudinal section.

11. The device according to claim 10, wherein said light sources and said light receivers are mounted on a holder surrounding the tobacco rod.

* * * * *